(12) United States Patent
Jones et al.

(10) Patent No.: US 10,049,444 B2
(45) Date of Patent: Aug. 14, 2018

(54) OPTICAL DEVICE FOR FUEL FILTER DEBRIS

(71) Applicant: Lockheed Martin Corporation, Bethesda, MD (US)

(72) Inventors: Mike Ivor Jones, Azle, TX (US); Kyle Alson McGehee, Aledo, TX (US); Eric White, Fort Worth, TX (US); Richard Parker McElveen, Jr., Saginaw, TX (US); Jennifer C. Byrne, Horsham, PA (US)

(73) Assignee: Lockheed Martin Corporation, Bethesda, MD (US)

( * ) Notice: Subject to any disclaimer, the term of this patent is extended or adjusted under 35 U.S.C. 154(b) by 204 days.

(21) Appl. No.: 15/080,856

(22) Filed: Mar. 25, 2016

(65) Prior Publication Data
US 2017/0278230 A1   Sep. 28, 2017

(51) Int. Cl.
*H04N 7/18* (2006.01)
*G06T 7/00* (2017.01)
*H04N 5/225* (2006.01)

(52) U.S. Cl.
CPC ............ *G06T 7/001* (2013.01); *G06T 7/0008* (2013.01); *H04N 5/2256* (2013.01); *H04N 7/183* (2013.01);
(Continued)

(58) Field of Classification Search
CPC ....... G06T 7/001; G06T 7/0008; H04N 5/2256; H04N 7/183; H04N 7/188
(Continued)

(56) References Cited

U.S. PATENT DOCUMENTS

| 6,630,996 B2 | 10/2003 | Rao et al. |
| 6,809,809 B2 | 10/2004 | Kinney et al. |

(Continued)

FOREIGN PATENT DOCUMENTS

| WO | 02066959 A2 | 8/2002 |
| WO | 2015192242 A1 | 12/2015 |

OTHER PUBLICATIONS

Eker, O. F. et al., "Filter Clogging Data Collection for Prognostics," Annual Conference of the Prognostics and Health Management Society 2013, https://www.phmsociety.org/node/1029, retrieved Aug. 8, 2017, pp. 1-9.

(Continued)

*Primary Examiner* — Farzana Hossain
(74) *Attorney, Agent, or Firm* — Baker Botts L.L.P.

(57) ABSTRACT

A fuel filter inspection method includes capturing an image of a fuel filter sample using an imaging device and sending the captured image to an image processor. The method further includes the image processor receiving the captured image, thresholding the captured image to generate a binary image, determining sizes for a plurality of particles present in the binary image, comparing the size of each of particle of the plurality of particles to a particle size threshold, and quantifying the number of particles of the plurality of plurality of particles with a size greater than the particle size threshold. The method further includes the image processor comparing the number of particles of the plurality of particles with a size greater than the particle size threshold to a particle count threshold, and modifying a graphical user interface to indicate a state of the fuel filter sample based on the comparison.

20 Claims, 9 Drawing Sheets

(52) U.S. Cl.
CPC ......... *H04N 7/188* (2013.01); *G06T 2200/24* (2013.01); *G06T 2207/10152* (2013.01); *G06T 2207/30108* (2013.01)

(58) Field of Classification Search
USPC .......................................................... 348/82
See application file for complete search history.

(56) References Cited

U.S. PATENT DOCUMENTS

| | | | |
|---|---|---|---|
| 7,998,115 B2 | 8/2011 | Bedingfield | |
| 8,720,499 B2 | 5/2014 | Kastner et al. | |
| 2007/0091309 A1* | 4/2007 | Kondo | G01N 21/95692 356/364 |
| 2008/0100840 A1* | 5/2008 | Oma | G01N 15/1463 356/339 |
| 2010/0045982 A1 | 2/2010 | Tsuneta et al. | |
| 2012/0105622 A1 | 5/2012 | Fedele | |
| 2014/0177932 A1 | 6/2014 | Milne et al. | |
| 2015/0009320 A1* | 1/2015 | Klein | G01N 21/958 348/128 |
| 2015/0211976 A1* | 7/2015 | David | B29C 67/0085 134/104.4 |
| 2015/0213616 A1 | 7/2015 | Kappeler et al. | |

OTHER PUBLICATIONS

Lapuerta, M. et al., "Diesel Particle Size Distribution Estimation from Digital Image Analysis," Aerosol Science and Technology, Nov. 30, 2010, pp. 369-381.

Extended European Search Report, Application No. 17160959.7, dated Aug. 23, 2017, 9 pages.

* cited by examiner

OPTICAL DEVICE FOR FUEL FILTER DEBRIS

TECHNICAL FIELD

The present disclosure relates in general to the inspection of particles or debris on a fuel filter such as an aircraft fuel filter.

BACKGROUND

Existing techniques for inspecting a fuel filter such as an aircraft fuel filter may require manual inspection by flight line personnel. A manual inspection may only provide qualitative and visual information. Further, manual inspections are susceptible to errors due to the subjectivity of the results and may not provide a scientifically quantifiable or consistent method for inspecting a fuel filter and/or deciding whether to perform costly fuel system flushing. Unnecessary fuel system flushing may lead to over-flushing and may increase the time and costs associated with fuel system maintenance.

Fuel filters may be saturated or covered with explosive or hazardous chemicals such as gasoline or jet fuel. Exposure to such hazardous chemicals may be dangerous to flight line personnel that inspects the fuel filters. It is desirable to provide a consistent method for inspecting or analyzing fuel filters while preventing harm to those performing the inspection or analysis.

SUMMARY

In one embodiment, an optical system includes an imaging device and an image processor. The imaging device is configured to enclose a fuel filter sample within the imaging device, to capture an image of the fuel filter sample, and to send the captured image to an image processor for processing. The image processor comprises a graphical user interface, a memory, and a processor. The memory is operable to store a particle size threshold and a particle count threshold. The processor is communicatively coupled to the graphical user interface and the memory, and is configured to receive the captured image from the imaging device and to threshold the captured image to generate a binary image. The processor is further configured to determine sizes for a plurality of particles present in the binary image, to compare the size of each particle of the plurality of particles to the particle size threshold, and to quantify the number of particles of the plurality of particles with a size greater than or equal to the particle size threshold. The processor is further configured to compare the number of particles of the plurality of particles with a size greater than or equal to the particle size threshold to the particle count threshold, to modify the graphical user interface to indicate the fuel filter sample is in a passed state when the number of particles of the plurality of particles with a size greater than or equal to the particle size threshold is less than the particle count threshold, and to modify the graphical user interface to indicate the fuel filter sample is in a failed state when the number of particles of the plurality of particles with a size greater than or equal to the particle size threshold is greater than or equal to the particle count threshold.

In another embodiment, a fuel filter inspection method comprises capturing an image of a fuel filter sample using an imaging device and sending the captured image to an image processor. The fuel inspection method further comprises receiving the captured image at the image processor and thresholding the captured image to generate a binary image. The fuel inspection method further comprises determining sizes for a plurality of particles present in the binary image, comparing the size of each of particle of the plurality of particles to a particle size threshold, and quantifying the number of particles of the plurality of plurality of particles with a size greater than or equal to the particle size threshold. The fuel inspection method further comprises comparing the number of particles of the plurality of particles with a size greater than or equal to the particle size threshold to a particle count threshold and modifying a graphical user interface to indicate a state of the fuel filter sample based on the comparison.

The present embodiment presents several technical advantages. The present embodiment discloses an optical system that provides high resolution imaging of particles trapped in fuel filters (e.g. aircraft fuel filters) and post-processing of acquired images to quantify particle size, orientation, and location. The optical system allows for classification of particle distribution by size or grades of filter debris. Further, the optical system may issue advisories (e.g., pass, reinspect, or fail) for fuel filters being measured and may generate documentation of image analysis such as a statistical analysis or trends. The optical system may be configured to provide functionality such as live image viewing, the ability to capture and analyze images, displaying analysis data to an operator, and allowing an operator to define tolerances and rules for inspecting fuel filters.

Further, the optical system may be configured to substantially reduce or eliminate shadowing while inspecting or analyzing fuel filters. The optical system may also be configured to reduce hazards such as the amount of heat that is present while inspecting or analyzing fuel filters. Reducing the amount heat that is present may provide a safer work environment when working with fuel filters covered with explosive or hazardous chemicals such as gasoline or jet fuel. In one embodiment, the optical system may be configured with a compact design which allows the optical system to be placed on a desk or table top.

Certain embodiments of the present disclosure may include some, all, or none of these advantages. These advantages and other features will be more clearly understood from the following detailed description taken in conjunction with the accompanying drawings and claims.

BRIEF DESCRIPTION OF THE DRAWINGS

For a more complete understanding of this disclosure, reference is now made to the following brief description, taken in connection with the accompanying drawings and detailed description, wherein the reference numerals represent like parts.

DETAILED DESCRIPTION

Disclosed herein are various embodiments for inspecting and analyzing fuel filters (e.g. aircraft fuel filters) using an optical system. The optical system allows an operator to inspect and analyze fuel filters that may be saturated or covered with explosive or hazardous chemicals. For example, the optical system may allow an operator to perform processes such as capturing images, processing captured images, quantifying the number of particles on a fuel filter, and providing pass/fail indications based on the number of particles on or in the fuel filter and predetermined or user defined rules.

In one embodiment, an optical system may be configured to enclose a fuel filter within an imaging device. The imaging device is configured to capture images of the fuel filter for image processing. The imaging device may employ backlighting to illuminate the fuel filter such that the particles on or in the fuel filter are visible and captured by the imaging device. The imaging device is configured to provide backlighting while reducing or eliminating the effects of shadowing within the imaging device. The imaging device is also configured to reduce potential hazards while imaging fuel filters. For example, the imaging device may be configured to provide low heat and/or ventilation while capturing images of the fuel filter. The optical system may be configured to provide live image viewing, to capture and analyze images, to display analysis data to an operator, and/or to allow an operator to define tolerances and rules for inspecting fuel filters.

Figure 1:
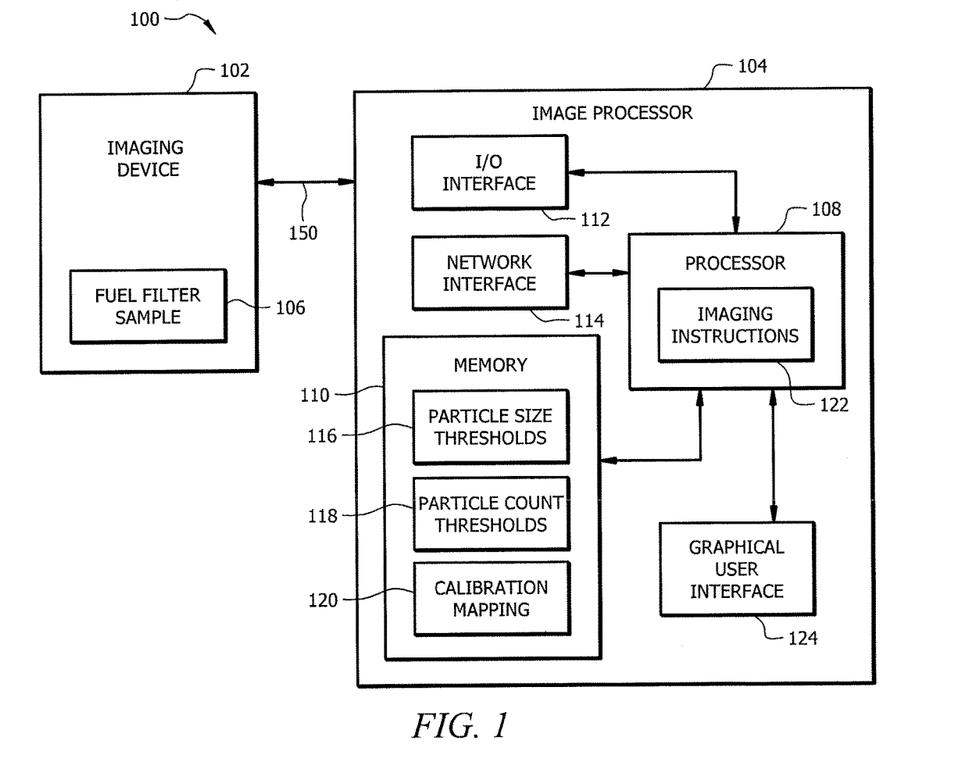
FIG. 1 illustrates a schematic diagram of an embodiment of an optical system for inspecting aircraft fuel filters.

FIG. 1 illustrates a schematic diagram of an embodiment of an optical system 100 for aircraft fuel filters. In an embodiment, optical system 100 is configured to isolate or enclose an aircraft fuel filter for inspection, to capture images of the aircraft fuel filter, and to perform imaging processing to inspect and analyze the aircraft fuel filter.

Optical system 100 comprises an imaging device 102 communicatively coupled to an image processor 104. FIG. 1 illustrates imaging device 102 and image processor 104 as discrete components, however, one of ordinary skill in the art would appreciate that imaging device 102 and image processor 104 may be integrated with each other into a single structure or device. Image processor 104 and imaging device 102 may be located in the same or in different geographical locations. For example, imaging device 102 and image processor 104 may be located in different geographical locations and configured to communicate remotely via a network connection. Optical system 100 may be configured as shown or in any other suitable configuration.

Imaging device 102 is configured to isolate or enclose a fuel filter sample 106 for inspection, to capture images of the fuel filter sample 106, and to communicate data (e.g. image data) to image processor 104 for processing. For example, imaging device 102 may be configured to allow the fuel filter sample 106 to be disposed within imaging device 102. Imaging device 102 may capture image data of the fuel filter sample 106 while providing a safe work environment for the operator. Imaging device 102 may be communicatively coupled to image processor 104 using a wired or wireless connection 150. Connection 150 is configured to allow data and/or control signals to be communicated between imaging device 102 and image processor 104. Any suitable wired or wireless connection 150 may be employed as would be appreciated by one of ordinary skill in the art upon viewing this disclosure. Imaging device 102 may further comprise networking or communication components (not shown) for communicating with image processor 104. Additional details for imaging device 102 are discussed in FIG. 2.

Fuel filter sample 106 is a fuel filter that screens out particles from a fuel system. Examples of particles include, but are not limited to, metals, dirt, dust, and rust. In an embodiment, fuel filter sample 106 is an aircraft fuel filter. Fuel filter sample 106 may diffuse transparently when illuminated by a light source (e.g. light source 208 in FIG. 2). Fuel filter sample 106 may comprise one or more layers of material. Examples of materials for fuel filter sample 106 include, but are not limited to, cotton and crêpe paper. Fuel filter sample 106 may be dry, partially saturated, or saturated with explosive or hazardous chemicals such as gasoline or jet fuel. Fuel filter sample 106 may be any shape, size, or thickness.

Image processor 104 is configured to communicate control signals to imaging device 102 and to receive data (e.g. image data) from imaging device 102. Examples of image processor 104 include, but are not limited to, notebook computers, tablet computers, desktop computers, mobile telephones, or any other suitable device as would be appreciated by one of ordinary skill in the art upon viewing this disclosure. In some embodiments, image processor 104 comprises a processor 108, a memory 110, an input/output (I/O) interface 112, a network interface 114, and a graphical user interface (GUI) 124. Image processor 104 may be configured as shown or in any other suitable configuration.

Memory 110 may comprise one or more disks, tape drives, or solid-state drives, and may be used as an over-flow data storage device, to store programs when such programs are selected for execution, and to store instructions and data that are read during program execution. Memory 110 may be volatile or non-volatile and may comprise read-only memory (ROM), random-access memory (RAM), ternary content-addressable memory (TCAM), dynamic random-access memory (DRAM), and static random-access memory (SRAM). Memory 110 is operable to store particle size thresholds 116, particle count thresholds 118, calibration mappings 120, and other data such as image data and particle data. Particle size thresholds 116 may be user-defined or predetermined thresholds that may be used to classify particles on fuel filter sample 106. Particle count thresholds 118 may be user-defined or predetermined thresholds that may be used for determining whether fuel filter sample 106 passes or fails an inspection. For example, particle count thresholds 118 may comprise a threshold that defines a maximum number of particles that are allowable on fuel filter sample 106 and that may be used to determine that fuel filter sample 106 fails an inspection when the number of particles measured on fuel filter sample 106 exceed the threshold and that fuel filter sample 106 passes the inspection when the number of particles on fuel filter sample 106 is less than the threshold. Calibration mappings 120 may provide a mapping between pixels and another units of measurement. For example, calibration mappings 120 may map from pixels to inches, centimeters (cm), millimeters (mm), microns or micrometers (μm), or any other units of measurement as would be appreciated by one of ordinary skill art upon viewing this disclosure.

Processor 108 may be implemented as one or more central processing unit (CPU) chips, logic units, cores (e.g. as a multi-core processor), field-programmable gate arrays (FPGAs), application specific integrated circuits (ASICs), or digital signal processors (DSPs). Processor 108 is communicatively coupled to and in signal communication with memory 110, I/O interface 112, network interface 114, and GUI 124. Processor 108 is configured to receive and transmit electrical signals among one or more of memory 110, I/O interface 112, network interface 114, GUI 124. The electrical signals may be used to send and receive data (e.g. image data from imaging device 102) or to control imaging device 102. For example, processor 108 may transmit electrical signals to operate one or more components (e.g. camera 202 and/or light source 208 in FIG. 2) of imaging device 102. Processor 108 may be communicatively coupled to one or more other devices (not shown). Processor 108 is configured to process data and may be implemented in hardware or software.

In FIG. 1, imaging instructions 122 are implemented as instructions (e.g. software code or firmware) stored in processor 108. Alternatively, imaging instructions 122 may be implemented as instructions stored in memory 110. The inclusion of imaging instructions 122 provides an improvement to the functionality of optical system 100, which effects a transformation of optical system 100 to a different state. Imaging instructions 122 are implemented by processor 108 to execute instructions for operating imaging device 102 and processing images captured by imaging device 102. Imaging instructions 122 comprise instructions for implementing various methods such as fuel filter inspection method 300 discussed in FIG. 3, live imaging method 600 discussed in FIG. 6, and data output generation method 800 discussed in FIG. 8. Imaging instructions 122 may be implemented using any suitable software or programming language as would be appreciated by one of ordinary skill in the art upon viewing this disclosure.

I/O interface 112 may comprise ports, transmitters, receivers, transceivers, or any other devices for transmitting and/or receiving data as would be appreciated by one of ordinary skill in the art upon viewing this disclosure. For example, I/O interface 112 may be configured to communicate data between imaging device 102 and image processor 104 (e.g. processor 108).

Network interface 114 may configured to enable wired and/or wireless communications and to communicate data through a network, system, and/or domain. For example, network interface 114 may comprise or may be integrated with a modem, a switch, a router, a bridge, a server, or a client. For example, image processor 104 may be configured to receive data from imaging device 102 via a network, which may allow image processor 104 to process the data remotely.

GUI 124 may be configured to provide present visual information to an operator of image processor 104. For example, GUI 124 may be employed to provide one or more interfaces such as interface 400 in FIGS. 4 and 5, interface 700 in FIG. 7, and interface 900 in FIG. 9. Examples of devices for implementing GUI 124 include, but are not limited to, a light emitting diode (LED) display, an organic LED (OLED) display, an active matric OLED (AMOLED), a projector display, a cathode ray (CRT) monitor, or any other suitable type of display as would be appreciated by one of ordinary skill in the art upon viewing this disclosure.

Figure 2:
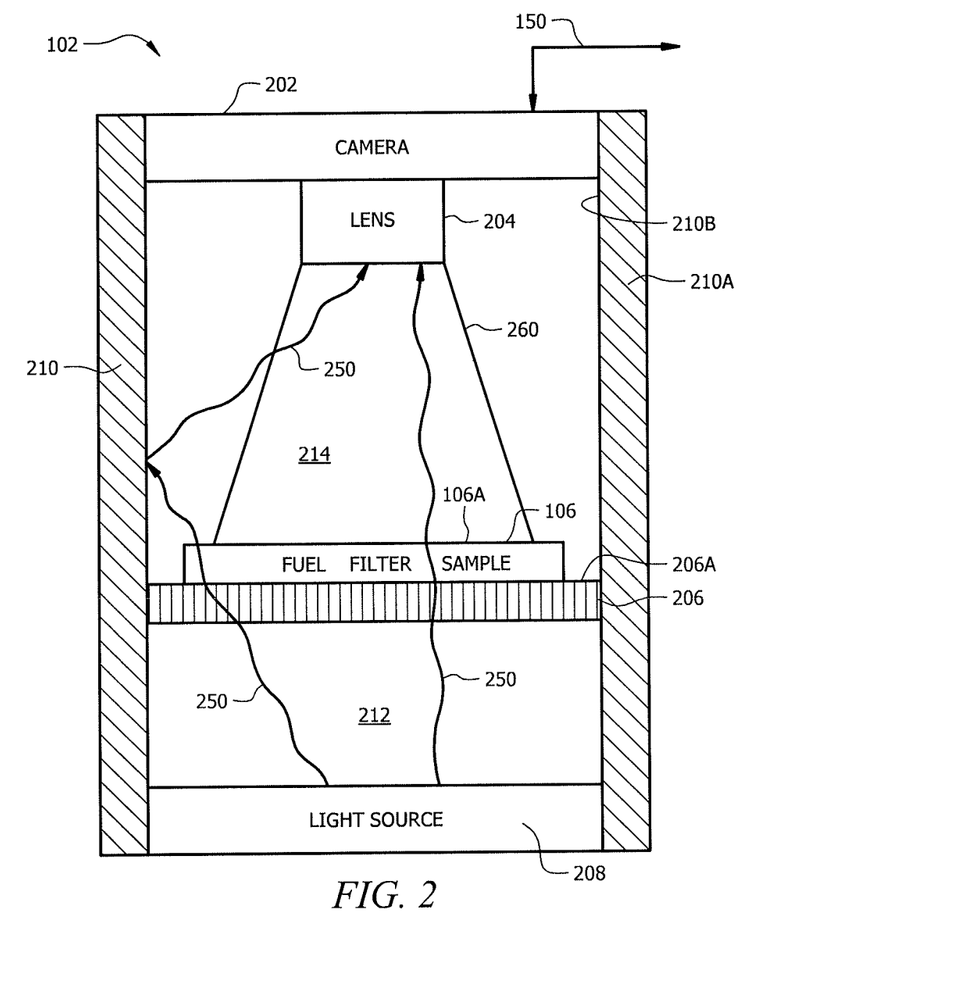
FIG. 2 illustrates a cutaway profile view of an embodiment of an imaging device of the optical system of FIG. 1.

FIG. 2 illustrates a cutaway profile view of an embodiment of an imaging device 102 of optical system 100. Imaging device 102 is configured to enclose fuel filter sample 106 that is disposed within imaging device 102, to provide backlight illumination to fuel filter sample 106, and to capture image data of fuel filter sample 106. Imaging device 102 may be configured as an omni-directional interior stage lighting device with a rectangular or cylindrical enclosure. In one embodiment, imaging device 102 may be configured as a diffuse-reflective containment system with a single light source 208 that is separated from an enclosed containment portion 214 of imaging device 102 by a translucent stage 206. In such a configuration, imaging device 102 may operate in a manner similar to an integrating sphere or an Ulbricht sphere.

In some embodiments, imaging device 102 may comprise camera 202, lens 204, translucent stage 206, and light source 208 at least partially enclosed within an enclosure 210. Imaging device 102 may be configured as shown or in any other suitable configuration as would be appreciated by one of ordinary skill in the art upon viewing this disclosure.

Enclosure 210 may be configured to support and position camera 202, lens 204, translucent stage 206, and light source 208. In an embodiment, enclosure 210 may be a rectangular or cylindrical structure. An example of material for constructing enclosure 210 includes, but is not limited to, white polycarbonate sheets. The side walls 210A of enclosure 210 may be opaque with any suitable thickness. For example, side walls 210A of enclosure 210 may be ⅛ inches thick. The interior face 210B of side walls 210A of enclosure 210 may be or may comprise a reflective surface that is configured to reflect light 250 within enclosure 210 to reduce the presence of shadows within enclosure 210. Light 250 may be reflected off of one or more interior surfaces (e.g. side walls 210A) of enclosure 210 to provide additional illumination to fuel filter sample 106, and thereby reduce the effects of shadowing on fuel filter sample 106. Enclosure 210 may comprise one or more removable walls or doors to allow an operator to dispose and position fuel filter sample 106 within enclosure 210.

Translucent stage 206 is configured to form a partition that divides enclosure 210 into a first enclosed portion 212 and a second enclosed portion 214. Enclosed portion 214 of enclosure 210 may be referred to as an enclosed containment or test portion and may be configured to operate as a integrating sphere to illuminate fuel filter sample 106 using backlighting from enclosed portion 212. In an embodiment, translucent stage 206 may be a white translucent structure. Translucent stage 206 is configured to allow light 250 from light source 208 in enclosed portion 212 of the enclosure 210 to pass through the translucent stage 206 to enclosed portion 214 of the enclosure 210. In an embodiment, translucent stage 206 comprises fiducial marks for positioning fuel filter sample 106 on the translucent stage 206. Examples of materials for translucent stage 206 include, but are not limited to, plexiglass and acrylic sheets. Translucent stage 206 is configured to support fuel filter sample 106 within enclosure 210. Translucent stage 206 may be any suitable size or thickness for supporting fuel filter sample 106. For example, translucent stage 206 may be ⅛ inches thick with an area of 28 inches by 28 inches. In an embodiment, translucent stage 206 may be oversized and have a surface 206A area that is greater than a surface 106A area of fuel filter sample 106. Translucent stage 206 may be or may be coated to comprise a coating that is chemically resistant. For example, translucent stage 206 may be chemically resistant to gasoline or jet fuel.

Camera 202 is configured to capture image data of fuel filter sample 106 and to send the image data to image processor 204 for processing or viewing. Camera 202 may be configured to capture image data continuously, at predetermined time intervals, or on-demand. For example, camera 202 may be configured to receive control signals from image processor 104 via connection 150 and to send the image data to image processor 104 via connection 150. Examples of camera 202 include, but are not limited to, a charge-coupled device (CCD) camera and a complementary metal-oxide semiconductor (CMOS) camera. Camera 202 is configured to provide a suitable resolution over an instantaneous field of view (IFOV) 260. For example, camera 202 may be a CCD camera with a resolution of 3384 by 2704 pixels to provide a resolution of 220 µm per IFOV 260 square pixel of the fuel filter sample 106. In this example, camera 202 may be configured with a pixel pitch of 3.69 µm square to provide a focal plane of 12.49 mm by 9.98 mm and a diagonal of about 16 mm. The focal plane of camera 202 may focus on a center portion of fuel filter sample 106. Assuming zero lens distortion, reducing the size of the focal plane may provide a magnification effect to camera 202. In the absence of lens aberrations a 3.69 µm square camera pixel may correspond to an IFOV 260 of fuel filter sample 106 of 179.48 µm. Alternatively, camera 202 may be any suitable camera with any suitable resolution to detect particles on or in fuel filter sample 106 as would be appreciated by one of ordinary skill in the art upon viewing this disclosure.

Lens 204 is communicatively coupled to camera 202 and configured to work in conjunction with camera 202 to detect particles on or in fuel filter sample 106. In an embodiment, camera 202 and lens 204 may be configured such that the exposure of camera 202 and the lens 204 are optimized to enhance contrast when capturing image data of fuel filter sample 106. Camera 202 and lens 204 may be positioned within enclosed portion 214 of enclosure 210 and vertically above fuel filter sample 106 and translucent stage 206. Lens 204 may be configured with any focal length and resolution to resolve features and particles on or in fuel filter sample 106. For example, lens 204 may be configured with a focal length of 16 mm and an F-number of 1.8. Alternatively, any suitable focal length and/or resolution may be employed as would be appreciated by one of ordinary skill in the art upon viewing this disclosure. An example of lens 204 includes, but is not limited to, a Schneider Cinegon 1.8/16 lens. Any suitable lens may be employed as would be appreciated by one of ordinary skill in the art upon viewing this disclosure. Lens 204 may be positioned at any suitable height above fuel filter 106. For example, assuming zero lens distortion with a focal length, f, and a magnification factor, M, the distance between lens 204 and fuel filter sample 106 may be determined by the following expression:

$$f\left(\frac{M+1}{M}\right).$$

Light source 208 is positioned in enclosed portion 212 of enclosure 210 and configured to provide light 250 (e.g. white light) to backlight fuel filter sample 106. Light source 208 is configured to provide stable light with relatively low heat output. Providing low heat may reduce potential fire or explosion hazards when inspecting fuel filter sample 106. Examples of light source 208 include, but are not limited to, LEDs. Light source 208 may comprise one or more bulbs (e.g. LED bulbs). For example, light source 208 may comprise rows of bulbs. Light source 208 may be configured in any configuration with any suitable light output as would be appreciated by one of ordinary skill in the art upon viewing this disclosure. In some embodiments, light source 208 may be controlled by image processor 104. For example, light source 208 may be configured to receive control signals from image processor 104 to turn on, off, or to modulate light source 208.

In some embodiments, imaging device 102 may comprise one or more ventilation components (not shown) configured to ventilate gases or fumes. Imaging device 102 may comprise exhaust fans, vents, or any other suitable components for venting or removing fumes as would be appreciated by one of ordinary skill in the art upon viewing this disclosure. Providing ventilation may reduce potential fire or explosion hazards when inspecting fuel filter sample 106.

Figure 3:
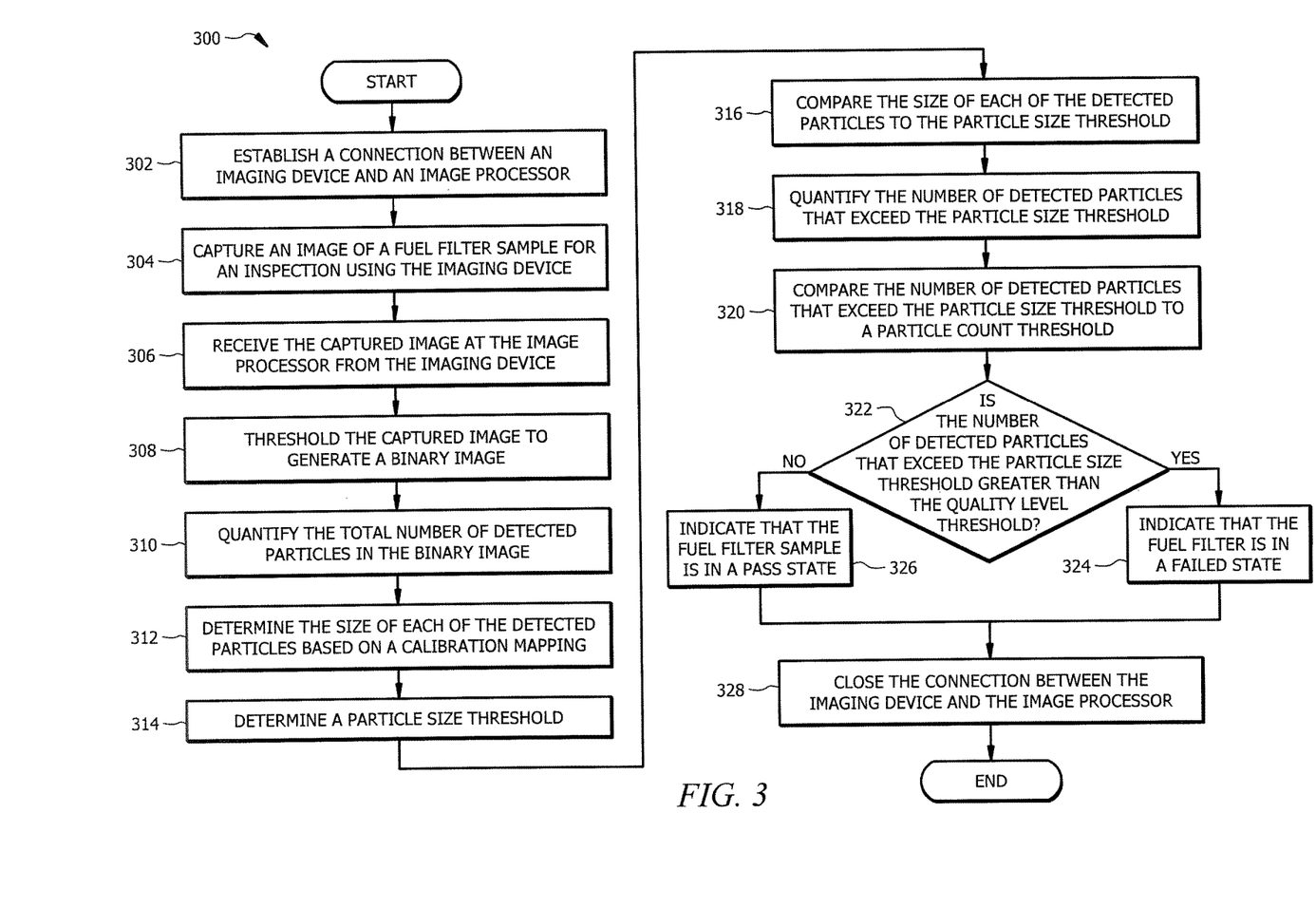
FIG. 3 illustrates a flowchart of an embodiment of a fuel filter inspection method for the optical system of FIG. 1.

FIG. 3 illustrates a flowchart of an embodiment of a fuel filter inspection method 300 for optical system 100. Method 300 may be employed by an operator to inspect a fuel filter sample 106 (e.g. an aircraft fuel filter). An operator may employ method 300 to determine whether fuel filter sample 106 passes inspection requirements based on the number of particles on fuel filter sample 106. The operator may dispose fuel filter sample 106 within imaging device 102 for inspection using image processor 104.

At step 302, a connection is established between imaging device 102 and image processor 104. For example, imaging device 102 and image processor 104 may communicate control signals and/or data signals to establish a session between imaging device 102 and image processor 104. In an embodiment, step 302 may be optional or may occur automatically when imaging device 102 and image processor 104 are powered up.

At step 304, imaging device 102 captures an image of fuel filter sample 106. For example, image processor 104 may send a control signal to imaging device 102 that indicates for imaging device 102 to capture an image of fuel filter sample 106 as image data. Imaging device 102 may capture one or more images of fuel filter sample 106 and may send the images as image data to image processor 104 in response to receiving the control signal from the image processor 104. In an embodiment, an operator may establish the connection and/or send the control signal using a capture and analyze command button 408 shown in FIGS. 4 and 5.

At step 306, image processor 104 receives the captured image as image data from imaging device 102. In an embodiment, image processor 104 may display the captured image to the operator, for example, in captured image window 402 shown in FIGS. 4 and 5. The image processor 104 may mask a portion of the captured image based on a region of interest. In an embodiment, image processor 104 may perform light condition corrections on the captured image. For example, the operator may employ image processor 104 to make brightness, gamma, and/or contrast adjustments.

At step 308, image processor 104 thresholds the captured image to generate a binary image. For example, image processor 104 may process the captured image by limiting the number of intensity levels that are present in the captured image. Any suitable thresholding technique may be employed as would be appreciated by one of ordinary skill in the art upon viewing this disclosure. In an embodiment, the resulting processed image may be generated with two intensity levels, for example, a first intensity level for particles and a second intensity level for the background (i.e. the fuel filter sample 106 material). Image processor 104 may display the binary image to the operator, for example, in processed image window 404 shown in FIGS. 4 and 5. In an embodiment, image processor 104 may add features to highlight the location and size of particles in the processed image. Image processor 104 may also be configured to perform noise correction processes such as removing a border from the processed image. Any suitable noise cancelling techniques may be employed as would be appreciated by one of ordinary skill in the art upon viewing this disclosure.

At step 310, image processor 104 quantifies the total number of detected particles in the binary image. For example, in the binary image each particle may be associated with an object having the first intensity and image processor 104 may count the number of particles that are present in the binary image. In an embodiment, image processor 104 may display or store the total number of detected particles in the binary image.

At step 312, image processor 104 determines the size of each of the detected particles based on calibration mapping 120. For example, image processor 104 may determine the number of pixels that are used to represent a particle and may use the calibration mapping 120 to convert the determined number of pixels to a unit of measurement such as mm or µm. In an embodiment, image processor 104 may also determine the position of each particle with respect to the binary image and may associate the determined position with the determined size of the particles. In other words, image processor 104 may also determine and store the position or coordinates of the particles with their respective particle size data.

At step 314, image processor 104 determines a particle size threshold 116. In an embodiment, the particle size threshold 116 may be provided by an operator. For example, the particle size threshold 116 may be input using a tolerance input field 414 shown in FIGS. 4 and 5. In another embodiment, the particle size threshold 116 may be predetermined or defined by inspection requirements stored in memory 110.

At step 316, image processor 104 compares the size of each of the detected particles to the particle size threshold 116. For example, image processor 104 may iterate through each of the detected particles and compare the size of each of the detected particles to particle size threshold 116 in order to determine whether each detected particle is greater than or less than the particle size threshold 116.

At step 318, image processor 104 quantifies the number of detected particles that exceed particle size threshold 116. In an embodiment, image processor 104 may display or store the number of detected particles that exceed particle size threshold 116. For example, the number of detected particles that exceed particle size threshold 116 may be displayed using number of particles indicator 416 shown in FIGS. 4 and 5.

At step 320, image processor 104 compares the number of detected particles that exceed particle size threshold 116 to particle count threshold 118. Image processor 104 compares the number of detected particles that exceed particle size threshold 116 to particle count threshold 118 to determine whether the amount of detected particles that exceed particle size threshold 116 is within the allowable number of particles for passing an inspection.

At step 322, image processor 104 determines whether the number of detected particles that exceed particle size threshold 116 exceeds particle count threshold 118. Image processor 104 proceeds to step 324 when the number of detected particles that exceed particle size threshold 116 exceeds particle count threshold 118. Otherwise, image processor 104 proceeds to step 326 when the number of detected particles that exceed particle size threshold 116 does not exceed particle count threshold 118.

At step 324, image processor 104 indicates that fuel filter sample 106 is in a failed state (i.e. fuel filter sample 106 has failed the inspection) in response to determining that the number of detected particles that exceed particle size threshold 116 exceeds particle count threshold 118. In other words, image processor 104 indicates that the number of detected particles that exceed particle size threshold 116 exceeds the maximum number of allowed particles to pass the inspection. Image processor 104 may indicate that fuel filter sample 106 is in the failed state using inspection result indicator 418 shown in FIGS. 4 and 5. An example of an interface displaying results for a fuel filter sample 106 that has failed the inspection is described in FIG. 5.

Returning to step 322, image processor 104 proceeds to step 326 when the number of detected particles that exceed particle size threshold 116 does not exceed particle count threshold 118. At step 326, image processor 104 indicates that fuel filter sample 106 is in a passed state (i.e. fuel filter sample 106 has passed the inspection) in response to determining that the number of detected particles that exceed particle size threshold 116 does not exceed the particle count threshold 118. In other words, image processor 104 indicates that the number of detected particles that exceed particle size threshold 116 is less than the maximum number of allowed particles to pass the inspection. Image processor 104 may indicate that fuel filter sample 106 is in the passed state using inspection result indicator 418 shown in FIGS. 4 and 5. An example of an interface displaying results for a fuel filter sample 106 that has passed the inspection is described in FIG. 4.

At step 328, which is an optional step, the operator closes the connection or session between imaging device 102 and image processor 104. For example, the operator may indicate to close the connection or session using a exit command button 412 shown in FIGS. 4 and 5.

Figure 4:
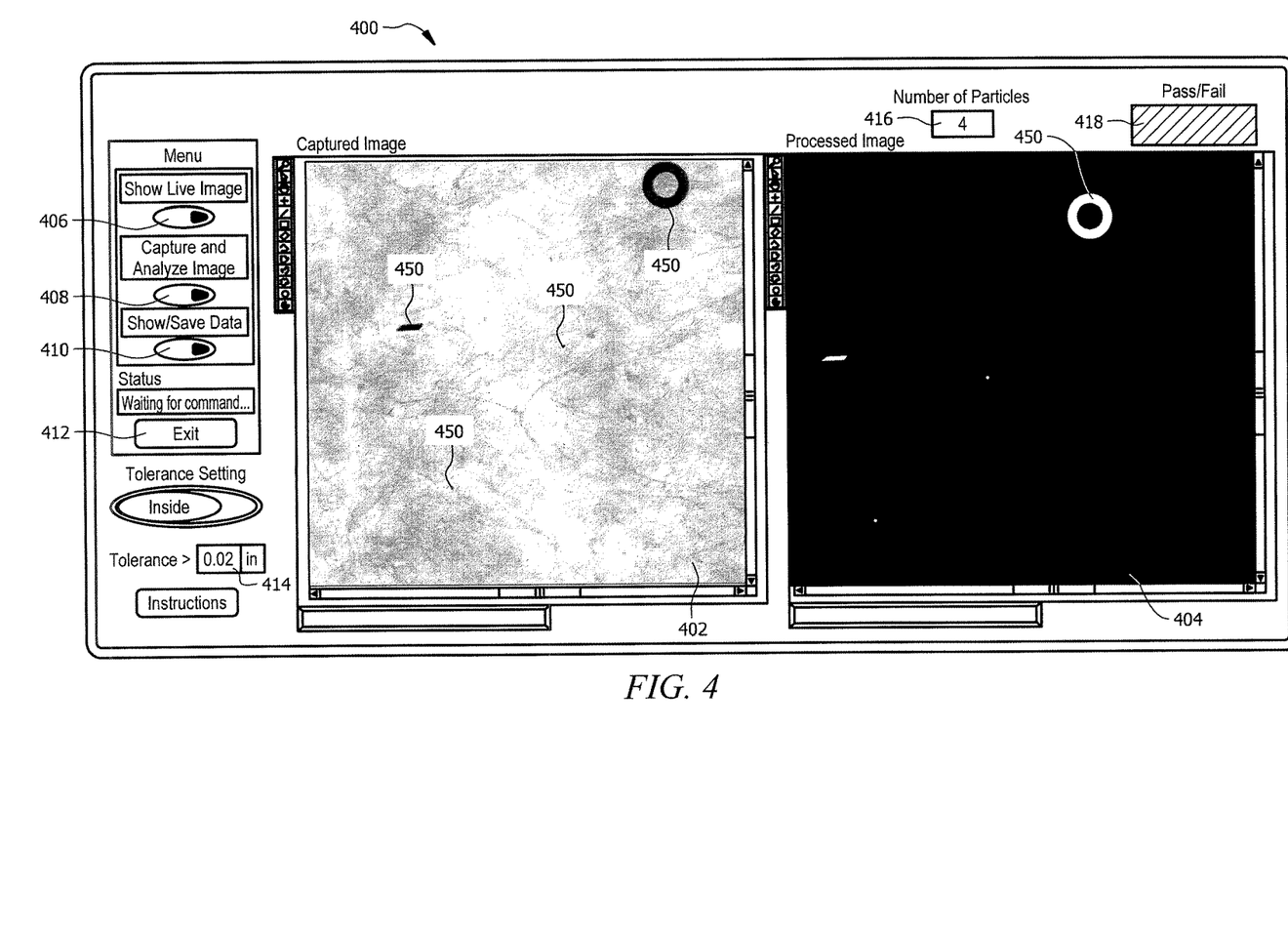
FIG. 4 illustrates an embodiment of an interface for displaying a fuel filter sample that passes an inspection.

FIG. 4 illustrates an embodiment of an interface 400 for displaying a fuel filter sample 106 that passes an inspection. Interface 400 may be implemented by GUI 124 and may be configured to receive inputs from an operator, to display image data, and/or to provide analysis data outputs to the operator. Interface 400 comprises a captured image window 402, a processed image window 404, a show live image command button 406, a capture and analyze command button 408, a show and save data command button 410, an exit command button 412, a tolerance input field 414, a number of particles indicator 416, and an inspection result indicator 418. Interface 400 may be configured as shown or in any other suitable configuration.

Captured image window 402 may be configured to display image data for captured images from imaging device 102. Captured image window 402 may be used by an operator to view particles 450 that are on or in fuel filter sample 106. In an embodiment, image processor 104 may add features (e.g. shapes or colors) to highlight the location and size of particles 450 within captured image window 402.

Processed image window 404 may be configured to display processed image data for captured images from imaging device 102. For example, processed image window 404 may display a binary image that is generated by thresholding a captured image. In an embodiment, image processor 104 may add features (e.g. shapes or colors) to highlight the location and size of particles 450 within processed image window 404. For example, image processor 104 may add features to indicate particles 450 that exceed particle size threshold 116.

Show live image command button 406 may be configured to allow an operator to send a control signal to imaging device 102 that indicates for imaging device 102 to provide continuous image data for image processing by image processor 104. For example, imaging device 102 may continuously capture and send the image data to image processor 104 in response to receiving the control signal. An example of a method for continuously capturing image data for processing is live imaging method 600 in FIG. 6. In some embodiments, a connection or session between imaging device 102 and image processor 104 may be established when an operator sends the control signal that indicates for imaging device 102 to provide continuous image data for image processing by image processor 104.

Capture and analyze command button 408 may be configured to allow an operator to send a control signal to imaging device 102 that indicates for imaging device 102 to provide a single image as image data for processing by image processor 104. For example, imaging device 102 may capture and send the image data for a single image to image processor 104 in response to receiving the control signal. An example of a method for processing the image data is fuel filter inspection method 300 in FIG. 3. In some embodiments, a connection or session between imaging device 102 and image processor 104 may be established when an operator sends the control signal that indicates for imaging device 102 to provide a single image as image data for processing by image processor 104.

Show and save data command button 410 may be configured to send a control signal to imaging device 102 that indicates to save image data or data that is associated with particles, captured images, and/or a processed images. For example, image processor 104 may store captured images, processed images, particle data (e.g. particle sizes), particle counts, and/or any other data into memory 110. An example of a method for saving and displaying data is data output generation method 800 in FIG. 8.

Exit command button 412 may be configured to send a control signal to imaging device 102 that indicates to terminate a connection, a session, or a stream of continuous image data between imaging device 102 and image processor 104.

Tolerance input field 414 may be an adjustable input field that allows an operator to set a particle size threshold 116. Number of particles indicator 416 may be an indicator configured to display the number of detected particle 450 or the number of detected particles 450 that exceeds particle count threshold 118. Inspection result indicator 418 may be an indicator configured to display whether a fuel filter sample 106 passes or fails an inspection based on particle size threshold 116 and particle count threshold 118. For example, inspection result indicator 418 may indicate a first color (e.g. green) when a fuel filter sample 106 passes an inspection and a second color (e.g. red) when a fuel filter sample 106 fails an inspection. Alternatively, inspection result indicator 418 may use any other color or indicators, such as, alphanumeric text, to indicate whether fuel filter sample 106 passes or fails an inspection.

In FIG. 4, the number of particles indicator 416 indicates that there are four particles 450 with a size that exceeds particle size threshold 116 in the captured image data from fuel filter sample 106. In this example, inspection result indicator 418 indicates that the number of particles 450 with a size that exceeds particle size threshold 116 is less than particle count threshold 118 and that fuel filter sample 106 passes the inspection.

Figure 5:
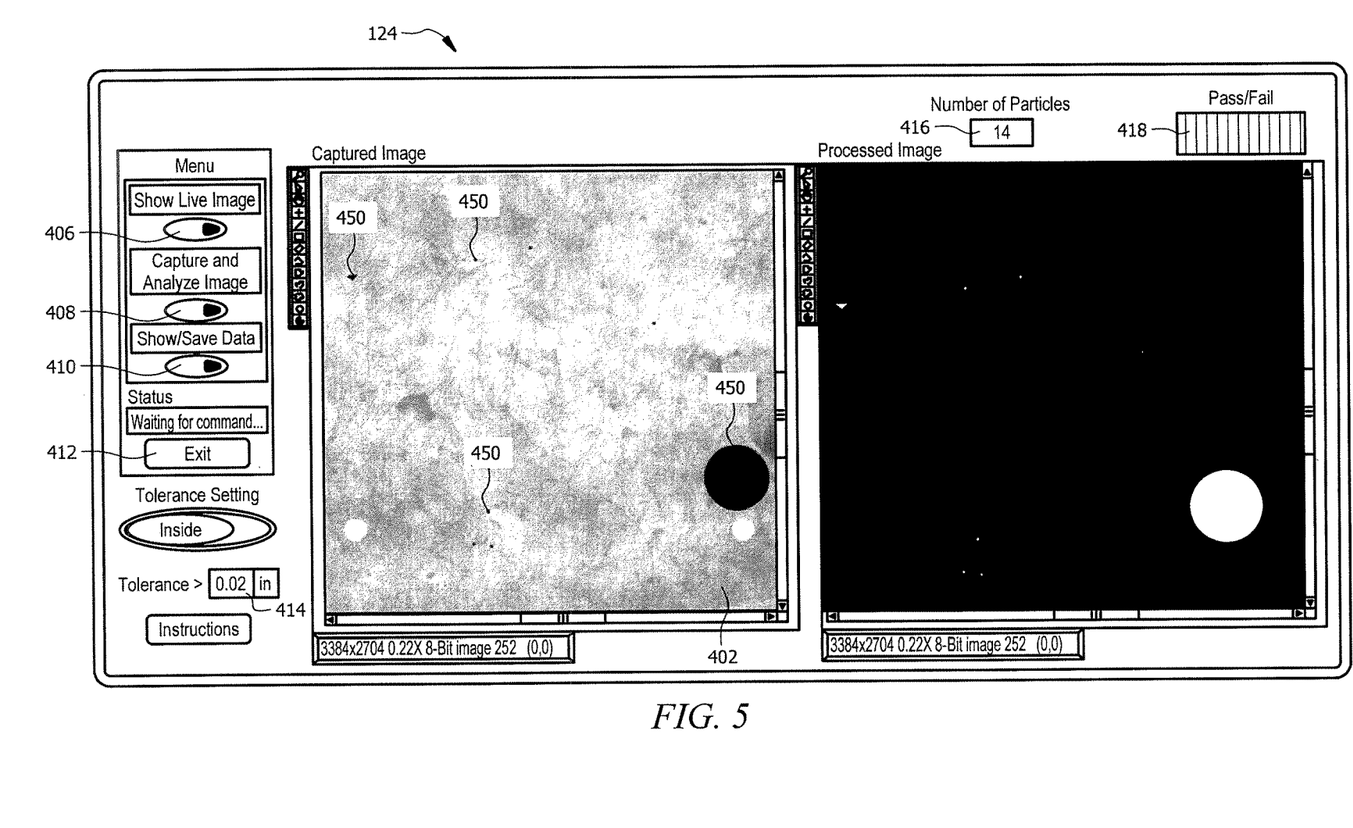
FIG. 5 illustrates an embodiment of interface for displaying a fuel filter sample that fails an inspection.

FIG. 5 illustrates an embodiment of interface 400 for displaying a fuel filter sample 106 that fails an inspection. In FIG. 5, number of particles indicator 416 indicates that there are 14 particles 450 with a size that exceeds particle size threshold 116 in the captured image data from fuel filter sample 106. In this example, inspection result indicator 418 indicates that the number of particles 450 with a size that exceeds particle size threshold 116 is less than particle count threshold 118 and that fuel filter sample 106 fails the inspection.

Figure 6:
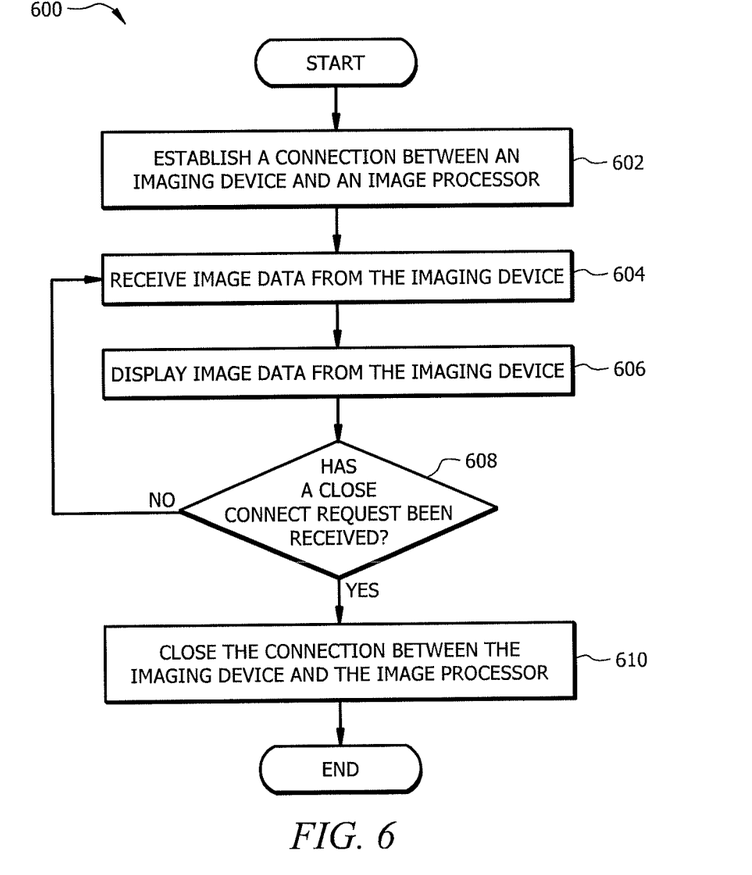
FIG. 6 illustrates a flowchart of an embodiment of a live imaging method for the optical system of FIG. 1.

FIG. 6 illustrates a flowchart of an embodiment of a live imaging method 600 for optical system 100. Method 600 may be employed by an operator to inspect fuel filter sample 106 using a continuous stream of images or image data. An operator disposes fuel filter sample 106 within imaging device 102 for inspection using image processor 104.

At step 602, a connection is established between imaging device 102 and image processor 104. For example, imaging device 102 and image processor 104 may communicate control signals and/or data signals to establish a session between imaging device 102 and image processor 104. In some embodiments, step 602 may be optional or may occur automatically when imaging device 102 and image processor 104 are powered up.

At step 604, image processor 104 receives image data from imaging device 102. In an embodiment, image processor 104 may send a control signal that indicates for imaging device 102 to capture an image of fuel filter sample 106 as image data. For example, the operator may send the control signal to imaging device 102 that indicates to establish a connection and/or for imaging device 102 to capture an image of fuel filter sample 106 using show live image command button 406 in FIGS. 4 and 5. Imaging device 102 may capture images of fuel filter sample 106 and may send the images as image data to image processor 104 in response to receiving the control signal from image processor 104. In an embodiment, imaging device 102 may be configured to continuously capture image data and to send the image data.

At step 606, image processor 104 displays the image data from imaging device 102. In an embodiment, image processor 104 may display the captured image to the operator, for example, in a captured image window 402 shown in FIGS. 4 and 5 or captured image window 702 shown in FIG. 7.

At step 608, image processor 104 determines whether a close connection request has been received. For example, image processor 104 may determine whether an operator requests to close the connection using exit command button 412 in FIGS. 4 and 5 or exit command button 704 in FIG. 7. Image processor 104 proceeds to step 610 when a close connection request has been received. Otherwise, image processor 104 returns to step 604 to continue receiving image data when the close connection request has not been received.

At step 610, which is an optional step, the operator closes the connection between imaging device 102 and image processor 104. For example, the operator may indicate to close the connection or session using a exit command button 412 shown in FIGS. 4 and 5 or exit command button 704 shown in FIG. 7.

Figure 7:
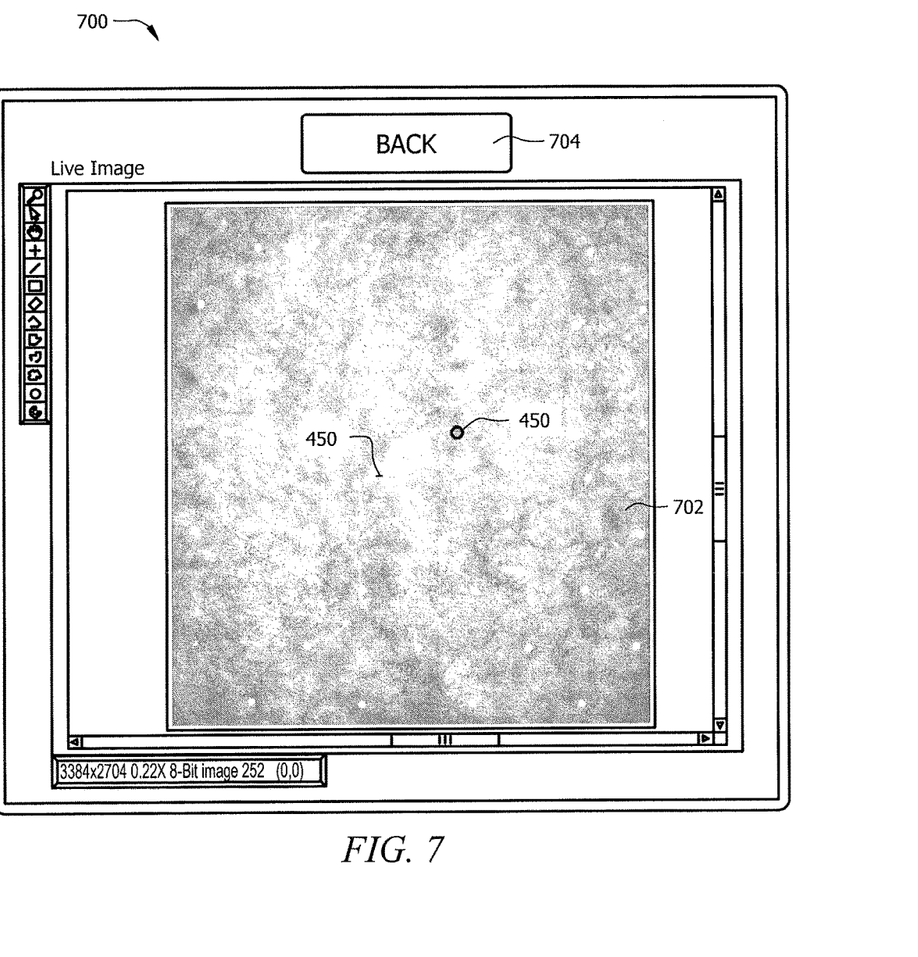
FIG. 7 illustrates an embodiment of an interface for displaying image data for an optical system employing a live imaging method.

FIG. 7 illustrates an embodiment of an interface 700 for displaying image data for optical system 100 employing live imaging method 600. Interface 700 may be implemented using GUI 124 and may be configured to receive inputs from an operator, to display image data, and/or to provide analysis data outputs to the operator. Interface 700 comprises captured image window 702 and exit command button 704. Interface 700 may be configured as shown or in any other suitable configuration.

Captured image window 702 may be configured to display image data or image data of captured images from imaging device 102. Captured image window 702 may be used by an operator to view particles 450 that are on or in fuel filter sample 106. Image processor 104 may add features to highlight the location and size of particles 450 within the captured image window 702. Exit command button 704 may be configured to send a control signal to imaging device 102 that indicates or requests to terminate a connection, a session, or a stream of continuous image data between imaging device 102 and image processor 104.

Figure 8:
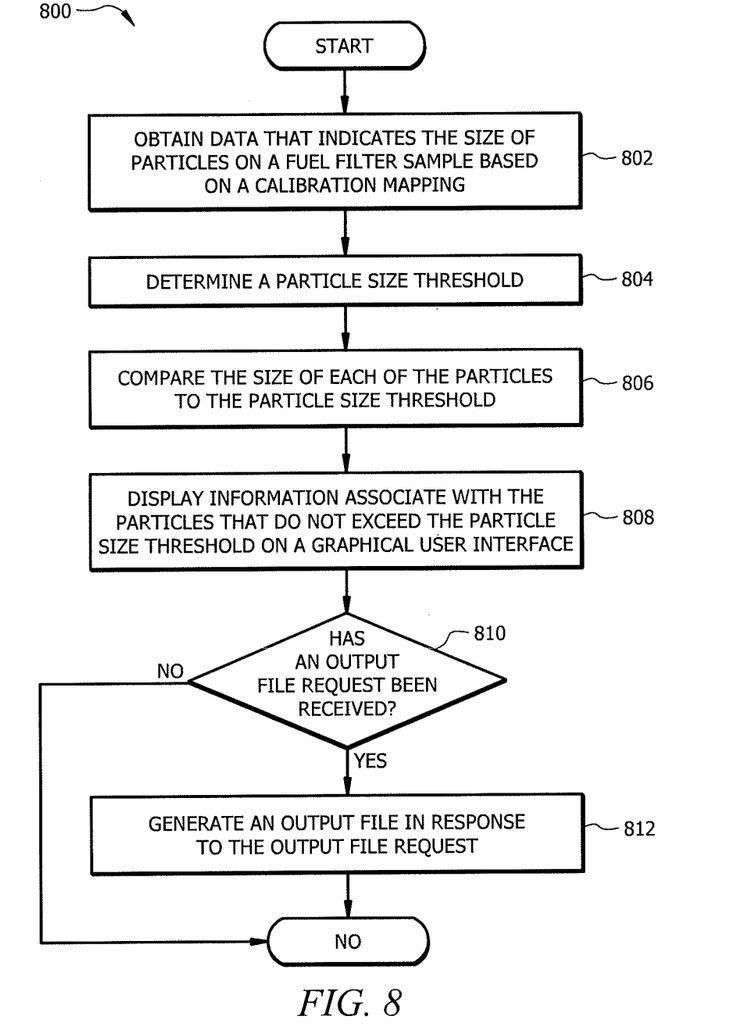
FIG. 8 illustrates a flowchart of an embodiment of a data output generation method for the optical system of FIG. 1.

FIG. 8 illustrates a flowchart of an embodiment of a data output generation method 800 for optical system 100. Method 800 may be employed by an operator to generate a data output for a fuel filter sample 106. For example, an operator may generate a data output file or display data associated with a fuel filter sample 106 using image processor 104.

At step 802, image processor 104 obtains data that indicates the size of particles on a fuel filter sample 106. The size of the particles may be a unit of measurement that is determined based on calibration mapping 120. Image processor 104 may obtain the data from an operator, memory 110, or from a fuel filter inspection method such as fuel filter inspection method 300 in FIG. 3.

At step 804, image processor 104 determines a particle size threshold 116. In an embodiment, particle size threshold 116 may be provided by an operator, for example, using tolerance input field 414 shown in FIGS. 4 and 5. In another embodiment, particle size threshold 116 may be predetermined or defined by inspection requirements stored in memory 110.

At step 806, image processor 104 compares the size of each of the particles to particle size threshold 116. For example, image processor 104 may iterate through each of the particles and compare the size of each of the particles to particle size threshold 116 to determine whether the particle is greater than or less than particle size threshold 116.

At step 808, image processor 104 displays information associated with the particles that do not exceed particle size threshold 116, for example, using GUI 124. Image processor 104 may display the number of particles that do not exceed particle size threshold 116, particles sizes, particle locations, and/or any other information associated with the particles that do not exceed particle size threshold 116. In another embodiment, image processor 104 may display information associated with the particles that exceed particle size threshold 116. Information associated with the particles that exceed particle size threshold 116 may be displayed in addition to or in place of the information associated with the particles that do not exceed particle size threshold 116.

At step 810, image processor 104 determines whether an output file request has been received. For example, an operator may request to store and/or display the data by making an output file request. An operator may indicate to make an output file request or to generate an output file using output file command button 908 shown in FIG. 9. Image processor 104 proceeds to step 812 when an output file request has been received. Otherwise, image processor 104 may terminate method 800 when the output file request has not been received.

At step 812, image processor 104 generates an output file in response to receiving the output file request. The output file may comprise data associated with particles such as the particle sizes or the number of particles that exceed or do not exceed particle size threshold 116. The output file may comprise other information including, but not limited to, a date, a time, an operator identifier, and a vehicle type. The output file may be generated and/or saved in any suitable format as would be appreciated by one of ordinary skill in the art upon viewing this disclosure. An example of an output format for an output file includes, but is not limited to, a comma separated values (csv) file.

Figure 9:
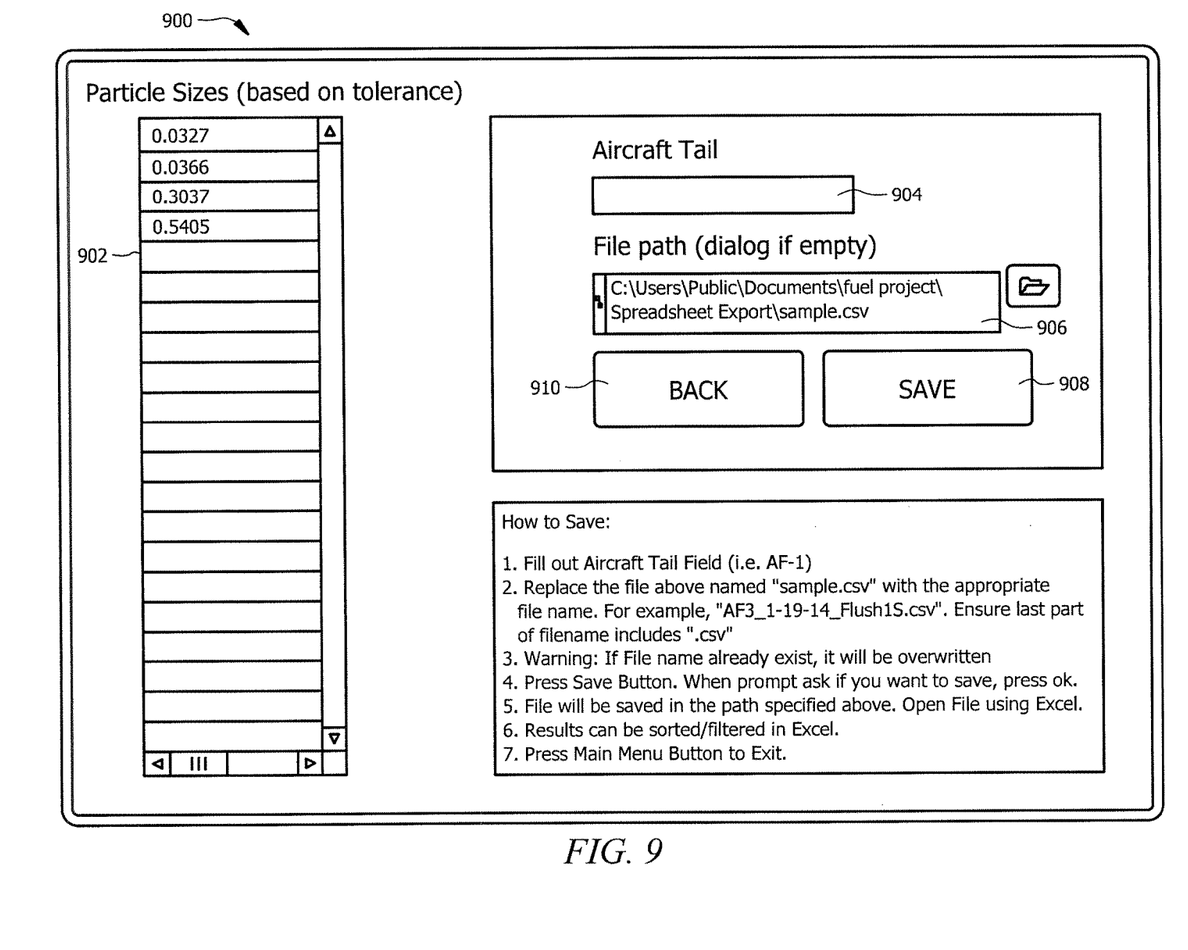
FIG. 9 illustrates an embodiment of an interface for the optical system of FIG. 1 employing a data output generation method.

FIG. 9 illustrates an embodiment of an interface 900 for optical system 100 employing a data output generation method 800. Interface 900 may be implemented by GUI 124 and may be configured to receive inputs from an operator, to display image data, and/or to provide analysis data outputs to the operator. In some embodiments, interface 900 comprises a particle size display chart 902, a vehicle type input field 904, a file path input field 906, an output file command button 908, and an exit command button 910. Interface 900 may be configured as shown or in any other suitable configuration.

Particle display chart 902 may be configured to display information associated with the particles on or in fuel filter sample 106, for example, information for particles that exceed particle size threshold 116 and/or information associated with the particles that do not exceed particle size threshold 116.

Vehicle type input field 904 may be configured to receive information that identifies a vehicle (e.g. an aircraft) that is associated with fuel filter sample 106. For example, vehicle type input field 904 may be used to input data for tracking vehicles associated with fuel filter samples 106. File path input field 906 may be configured to receive a file path for storing information associated with the particles, for example, particles that exceed particle size threshold 116 and/or information associated with the particles that do not exceed particle size threshold 116 in memory 110.

Output file command button 908 may be configured to allow an operator to indicate or request to save the particle data, the vehicle type input field 904 data, and/or any other data at the location specified by the file path input field 906. Exit command button 910 may be configured to send a control signal to imaging device 102 that indicates or requests to terminate a connection, a session, or process between imaging device 102 and image processor 104.

While several embodiments have been provided in the present disclosure, it should be understood that the disclosed systems and methods might be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

As another example, while certain embodiments have been disclosed in relation to aircraft fuel filters, the embodiments described herein may be used to inspect any appropriate filter.

In addition, techniques, systems, subsystems, and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component whether electrically, mechanically, or otherwise. Other examples of changes, substitutions, and alterations are ascertainable by one skilled in the art and could be made without departing from the spirit and scope disclosed herein.

To aid the Patent Office, and any readers of any patent issued on this application in interpreting the claims appended hereto, applicants note that they do not intend any of the appended claims to invoke 35 U.S.C. 112(f) as it exists on the date of filing hereof unless the words "means for" or "step for" are explicitly used in the particular claim.

The invention claimed is:

1. A system, comprising:
an imaging device configured to:
  enclose a fuel filter sample within the imaging device; and
  capture an image of the fuel filter sample; and
an image processor comprising:
  a graphical user interface;
  a memory configured to store a particle size threshold and a particle count threshold; and
  a processor communicatively coupled to the graphical user interface and the memory, the processor configured to:
    receive the captured image from the imaging device;
    threshold the captured image to generate a binary image;
    determine sizes for a plurality of particles present in the binary image;
    compare the size of each particle of the plurality of particles to the particle size threshold;
    quantify the number of particles of the plurality of particles with a size greater than the particle size threshold;
    compare the number of particles of the plurality of particles with a size greater than the particle size threshold to the particle count threshold;
    modify the graphical user interface to indicate the fuel filter sample is in a passed state when the number of particles of the plurality of particles with a size greater than the particle size threshold is less than the particle count threshold; and
    modify the graphical user interface to indicate the fuel filter sample is in a failed state when the number of particles of the plurality of particles with a size greater than the particle size threshold is greater than or equal to the particle count threshold.

2. The system of claim 1, wherein the graphical user interface is configured to display at least one of the captured image and the binary image.

3. The system of claim 1, wherein capturing the image of the fuel filter sample comprises the imaging device providing backlighting to the fuel filter sample.

4. The system of claim 1, wherein the imaging device comprises:
a light source;
a first enclosed portion; and
a second enclosed portion;
wherein the fuel filter sample is located in the second enclosed portion; and
wherein the light source is located in the first enclosed portion and configured to provide backlighting to the fuel filter sample located in the second enclosed portion.

5. The system of claim 1, wherein:
the processor is configured to send a control signal to the imaging device that indicates for the imaging device to capture the image of the fuel filter sample; and
the imaging device is configured to send the captured image to the processor in response to the control signal.

6. The system of claim 1, wherein the imaging device comprises a chemically resistant translucent stage that supports the fuel filter sample.

7. The system of claim 1, wherein the imaging device comprises an enclosure with a plurality of reflective interior surfaces configured to reflect light within the imaging device.

8. The system of claim 1, wherein:
the processor is further configured to generate an output file in response to an output file request; and
the output file comprises information associated with at least one of the plurality of particles present in the binary image.

9. The system of claim 1, wherein the processor is configured to modify the graphical user interface to display information associated with at least one of the plurality of particles present in the binary image.

10. The system of claim 1, wherein determining sizes for the plurality of particles present in the binary image comprises using a calibration mapping that maps pixels to a unit of measurement.

11. A fuel filter inspection method comprising:
enclosing a fuel filter sample within an imaging device;
capturing an image of the fuel filter sample using the imaging device;
sending, by the imaging device, the captured image to an image processor;
receiving the captured image at the image processor;
thresholding, by the image processor, the captured image to generate a binary image;
determining, by the image processor, sizes for a plurality of particles present in the binary image;
comparing, by the image processor, the size of each of particle of the plurality of particles to a particle size threshold;
quantifying, by the image processor, the number of particles of the plurality of plurality of particles with a size greater than the particle size threshold;
comparing, by the image processor, the number of particles of the plurality of particles with a size greater than the particle size threshold to a particle count threshold; and
modifying, by the image processor, a graphical user interface to indicate a state of the fuel filter sample based on the comparison.

12. The method of claim 11, further comprising modifying, by the image processor, the graphical user interface to display at least one of the captured image and the binary image.

13. The method of claim 11, wherein capturing the image of the fuel filter sample comprises providing backlighting to the fuel filter sample by the imaging device.

14. The method of claim 11, further comprising sending, by the image processor, a control signal to the imaging device that indicates for the imaging device to capture the image of the fuel filter sample.

15. The method of claim 11, further comprising modifying, by the image processor, the graphical user interface to display information associated with at least one of the plurality of particles present in the binary image.

16. The method of claim 11, wherein determining the size for the plurality of particles present in the binary image comprises using, by the image processor, a calibration mapping that maps pixels to a unit of measurement.

17. An apparatus comprising:
a graphical user interface;
a memory configured to store a particle size threshold and a particle count threshold; and a processor communicatively coupled to the graphical user interface and the memory, the processor configured to:
receive a captured image of a fuel filter sample from an imaging device, wherein the captured image is produced by an imaging device enclosing the fuel filter sample;
threshold the captured image to generate a binary image;
determine sizes for a plurality of particles present in the binary image;
compare the size of each particle of the plurality of particles to the particle size threshold;
quantify the number of particles of the plurality of particles with a size greater than the particle size threshold;
compare the number of particles of the plurality of particles with a size greater than the particle size threshold to the particle count threshold;
modify the graphical user interface to indicate the fuel filter sample is in a passed state when the number of particles of the plurality of particles with a size greater than the particle size threshold is less than the particle count threshold; and
modify the graphical user interface to indicate the fuel filter sample is in a failed state when the number of particles of the plurality of particles with a size greater than the particle size threshold is greater than or equal to the particle count threshold.

18. The apparatus of claim 17, wherein the graphical user interface is configured to display at least one of the captured image and the binary image.

19. The apparatus of claim 17, wherein the processor is further configured to send a control signal to the imaging device that indicates for the imaging device to capture the image of the fuel filter sample.

20. The apparatus of claim 17, wherein determining the sizes for the plurality of particles present in the binary image comprises using a calibration mapping that maps pixels to a unit of measurement.

* * * * *